United States Patent [19]
Palti

[11] Patent Number: 5,368,028

[45] Date of Patent: * Nov. 29, 1994

[54] SYSTEM FOR MONITORING AND CONTROLLING BLOOD AND TISSUE CONSTITUENT LEVELS

[75] Inventor: Yoram Palti, Haifa, Israel

[73] Assignee: CB-Carmel Biotechnology Ltd., Haifa, Israel

[ * ] Notice: The portion of the term of this patent subsequent to Apr. 7, 2009 has been disclaimed.

[21] Appl. No.: 77,893

[22] Filed: Jun. 16, 1993

Related U.S. Application Data

[60] Continuation of Ser. No. 832,248, Feb. 7, 1992, abandoned, which is a continuation-in-part of Ser. No. 816,303, Dec. 27, 1991, Pat. No. 5,190,041, which is a division of Ser. No. 392,828, Aug. 11, 1989, Pat. No. 5,101,814.

[51] Int. Cl.$^5$ ............................ A61B 5/00; A61M 5/00
[52] U.S. Cl. ........................................ 128/635; 604/31; 604/50; 604/66
[58] Field of Search ................ 128/635; 604/31, 50, 604/66, 67; 204/403, 415

[56] References Cited

U.S. PATENT DOCUMENTS

| | | |
|---|---|---|
| 3,837,339 | 9/1974 | Aisenberg et al. . |
| 4,136,101 | 1/1979 | Kazan . |
| 4,140,963 | 2/1979 | Rao et al. . |
| 4,332,893 | 6/1982 | Rosenberg . |
| 4,352,883 | 10/1982 | Lim . |
| 4,353,888 | 10/1982 | Sefton . |
| 4,374,987 | 2/1983 | Singh et al. . |
| 4,375,987 | 3/1983 | Lange et al. . |
| 4,409,331 | 10/1983 | Lim . |
| 4,436,094 | 3/1984 | Cerami . |
| 4,633,878 | 1/1987 | Bombardieri . |
| 4,663,286 | 5/1987 | Tsang . |
| 4,677,982 | 7/1987 | LLinas et al. . |
| 4,689,293 | 8/1987 | Goosen et al. . |
| 4,703,756 | 11/1987 | Gough et al. . |
| 4,704,029 | 11/1987 | Van Heuvelen . |
| 4,798,786 | 1/1989 | Tice et al. . |
| 4,803,168 | 2/1989 | Jarvis . |
| 4,822,336 | 4/1989 | DiTraglia . |
| 4,919,141 | 4/1990 | Zier et al. . |
| 5,101,814 | 4/1992 | Palti .................... 128/635 |

FOREIGN PATENT DOCUMENTS

| | | |
|---|---|---|
| 3713060 | 11/1987 | Germany . |
| 62213760 | 3/1986 | Japan . |

OTHER PUBLICATIONS

Akaike, N. et al, "Electrical Responses of Frog Taste Cells To Chemical Stimuli", J. Physiol. (1976), 254, pp. 87–107.

Altman, J. et al, "Long-Term Plasma Glucose Normalization In Experimental Diabetic Rats With Macroencapsulated Implants Of Benign Human Insulinomas", Diabetes, vol. 35, Jun. 1986.

Amsterdam, A. et al, "Structural and Functional Characterization of Isolated Pancreatic Cells", Proc. Nat. Acad. Sci. USA, vol. 69, No. 10, pp. 3028–3032, Oct. 1972.

Amsterdam, A. et al, "Studies On Dispersed pancreatic Exocrine Cells", Journal of Cell Biology, vol. 63, (1974) pp. 1037–1056.

(List continued on next page.)

*Primary Examiner*—Lee S. Cohen
*Attorney, Agent, or Firm*—Bryan Cave

[57] ABSTRACT

Systems are disclosed which utilize implanted chemosensitive living cells to monitor tissue or blood concentration levels of chemicals. The implanted cells produce a detectable electrical, optical or chemical signal in response to changes in concentration in surrounding medium. The signal is then detected and interpreted to give a reading indicative of blood concentration levels. Capsules containing chemo-sensitive cells and electrodes for detecting electrical activity are also disclosed. Methods of monitoring the concentration are also described utilizing the systems and capsules disclosed.

26 Claims, 9 Drawing Sheets

OTHER PUBLICATIONS

Atwater, I. et al, "Three K Channels in Human Pancreatic B-Cells Identical to Those in Rat B-Cells", Biophysical Journal, M-AM-A9, vol. 55, (1989).

Avenet, P. et al, "Patch-Clamp Study of Isolated Taste Receptor Cells of the Frog", J. Membrane Biol. 97, pp. 223-240 (1987).

Brown, J. et al, "Fetal Pancreas Transplantation for Reversal of Streptozotocin-induced Diabetes in Rats", Diabetes, vol. 25, No. 1, pp. 56-64.

Carrington, C. A. et al "Five New Insulin-Producing Cell Lines Wtih Differing Secretory Properties", J. Endocr. (1986) 109, pp. 193-200.

Charles, R. et al "A Multi-Center Study of the Laserdish Electrode", Cardiac Pacing and Electrophysiology, Proceedings of the VIIIth World Symposium on Cardiac Pacing and Electrophysiology, Jun. 7-11, 1987.

Eddlestone, G. T. et al "Electrical Coupling Between Cells in Islets of Langerhans From Mouse", J. Membrane Biol. 77, pp. 1-14, (1984).

Grinvald, A. et al "Optical Imaging of Neuronal Activity" Physiological Review, vol. 68, No. 4, Oct. 1988.

Gross, David et al "Optical Imaging of Cell Membrane Potential Changes Induced By Applied Electric Fields" Biophysical Journal, vol. 50, pp. 339-348 (1986).

Hidalgo, J. et al "Calcium Currents in Rat Pancreatic B-Cells in Culture", Biophysical Journal, W-PM-A3 vol. 55, (1989).

Howard, R. B. et al. "The Enzymatic Preparation of Isolated Intact Parenchymal Cells From Rat Liver", The Journal of Cell Biology, vol. 35, pp. 675-684 (1967).

Meda, P. et al "The Topograhy of Electrical Synchrony Among B-Cells in the Mouse Islet of Langerhans", Quarterly Journal of Experimental Physiology (1984) 69, pp. 719-735.

Palade, G. E. et al "Structure, Chemistry and Function of the Pancreatic Exocrine Cell".

Pressel, D. et al "Ion Channel Currents in Canine Pancreatic Islet B Cells", Biophysical Journal, W-Pos 221, vol. 55, (1989).

Ricordi, C. et al "A Method for the Mass Isolation of Islets From the Adult Pig Pancreas", Diabetes, vol. 35 (Jun. 1986).

Scott, A. M. et al "A Method for the Simultaneous Measurement of Insulin Release and B Cell Membrane Potential in Single Mouse Islets of Langerhans", Diabetologia (1981) 21:470-475.

Sorenson, R. L. et al "Dissociation of Glucose Stimulation of Somatostatin and Insulin Release From Glucose Inhibition of Glucagon Release in the Isolated Perfused Rat Pancreas", Diabetes, vol. 32 (Jun. 1983).

Schmidt, R. E. et al "The Effect of Pancreatic Islet Transplantation and Insulin Therapy on Experimental Diabetic Automomic Neuropathy", Diabetes, vol. 32 (Jun. 1983).

Tonosaki K. et al. "Voltage-and-Current-Clamp Recordings of the Receptor Potential in Mouse Taste Cell", Brain Research, 445 (1988) pp. 363-366.

Winkle, R. A. et al "Comparison of Defibrillation Efficacy in Humans Using a New Catheter and Superior Vena Cava Spring-Left Ventricular Patch Electrodes", JACC, vol. 11, No. 2 Feb. 1988:365-70.

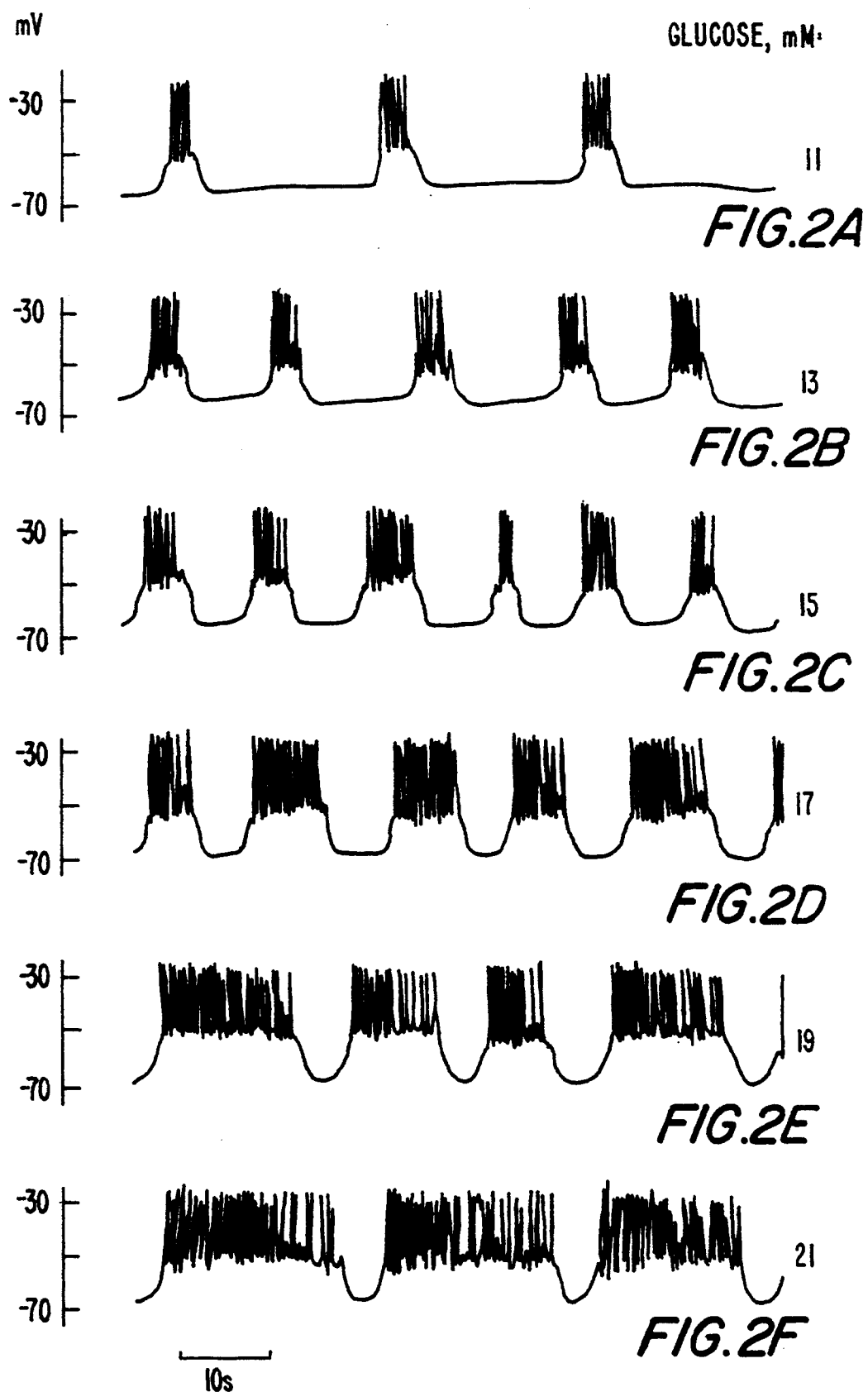

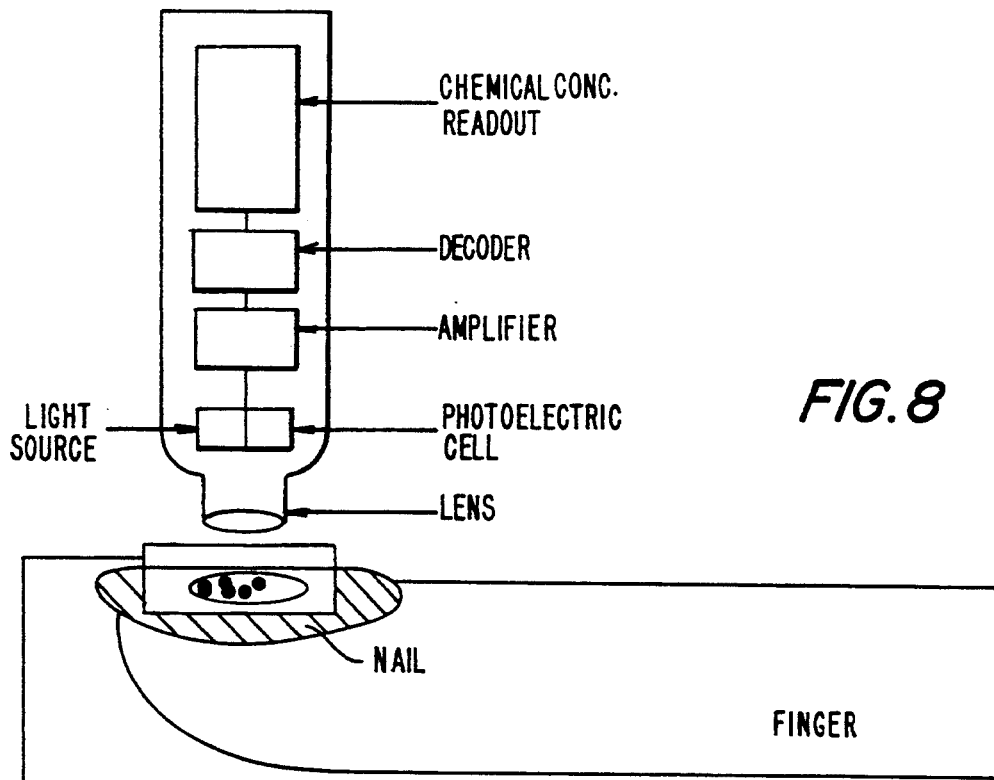
FIG. 8
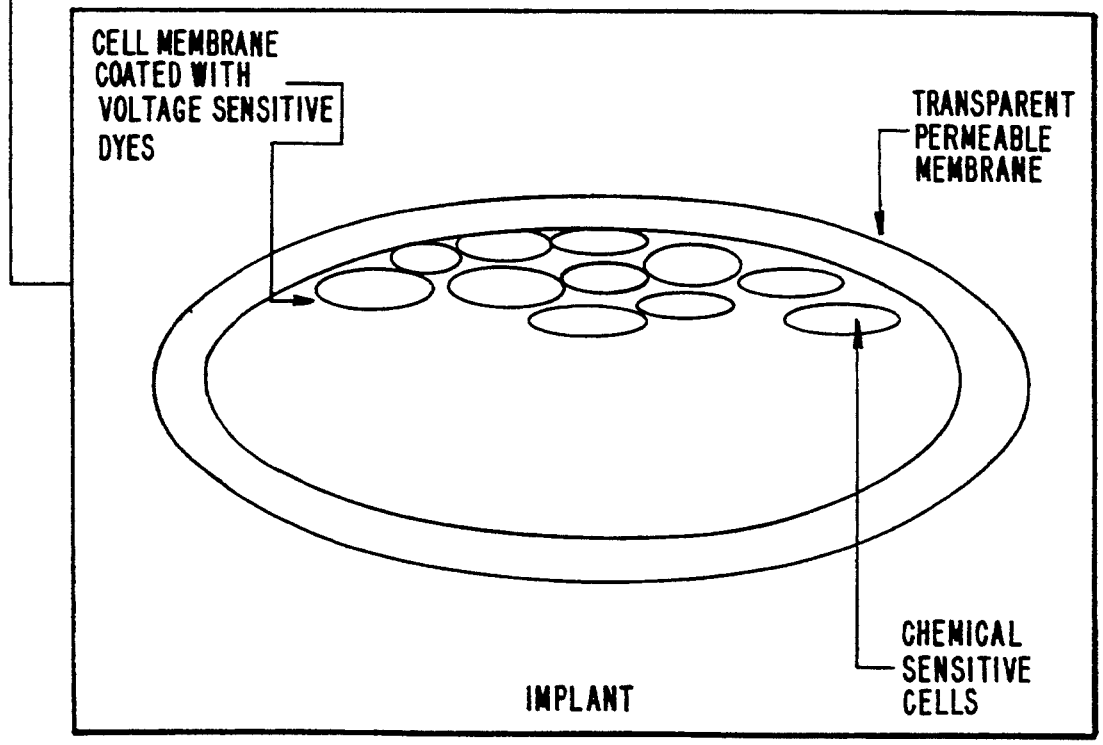

SYSTEM FOR MONITORING AND CONTROLLING BLOOD AND TISSUE CONSTITUENT LEVELS

This is a continuation, of U.S. application Ser. No. 07/832,248 filed Feb. 7, 1992, now abandoned, which is a continuation-in-part of U.S. application Ser. No. 07/816,303, filed Dec. 27, 1991, now U.S. Pat. No. 5,190,041, which is a divisional of U.S. application Ser. No. 07/392,828, filed Aug. 11, 1989, now U.S. Pat. No. 5,101,814.

FIELD OF THE INVENTION

The present invention relates to means for monitoring and controlling the level of various chemical constituents in the blood and in bodily tissues. Particularly, the invention relates to a system for monitoring constituent concentrations with appropriate chemo-sensitive living cells that produce an electrical, optical, or chemical response to the levels of the chemicals in the surrounding medium. These levels can then be used, for example, to determine the constituent concentration and on that basis a chemical can be administered or another correcting measure can be taken.

BACKGROUND OF THE INVENTION

Numerous diseases and pathophysiological states are associated with deviations from normal concentrations of constituents in the blood and bodily tissues. For instance, an elevation of blood and tissue potassium ion and urea levels is associated with many kidney diseases; an elevation of blood glucose levels is associated with diabetes; lowering of thyroxin levels is associated with various thyroid gland malfunctions.

In many cases the level of the chemical constituents of the body as a whole or of particular tissues or the blood are actively controlled. Such control requires that there be a sensor that responds to changes in constituent concentrations, partial pressure, or the like, and that the sensor relays the constituent information to appropriate cells or tissues that can act to correct the situation. These sensors are usually living cells that are specialized to react to a specific chemical stimulus. In some cases the cell sensors activate a nerve that transmits the constituent information to appropriate tissues that generate the correction. For example an increase in blood carbon dioxide levels activates sensors that in turn activate a response that eventually results in a change in lung ventilation.

In some cases sensor cells themselves act to correct the constituent levels. For example, alfa and beta cells of the pancreas respond to changes in the constituent levels and then secrete various hormones which affect, among other things, the constituent level.

The blood levels of chemical constituents such as sex-linked hormones (estrogens, androgens, etc.); metabolism-controlling hormones (thyroid, growth hormones, etc.); and steroids, etc., are also detected by cells with special sensitivity to a specific substance or group of substances. The detection of these hormones then results in a corrective response being generated.

Occasionally sensors respond to a change in constituent concentration by relaying information to the nervous system, but such information is not acted upon. For example, the chemo-sensors in the taste buds or the olfactory (smell) systems relay information to the nervous system but no corrective measures necessarily result. Nonetheless, these types of cells are excellent chemo-sensors.

As discussed above, an elevation of blood glucose levels is associated with diabetes. Diabetes is a metabolic disorder that afflicts tens of millions of people in the developed countries of the world, with many millions more probably affected in underdeveloped nations. Diabetes results from the inability of the body to properly utilize and metabolize carbohydrates, particularly glucose. Normally, the finely-tuned balance between glucose in the blood and glucose in bodily tissue cells is maintained by insulin, a hormone produced by the pancreas which controls, among other things, the transfer of glucose from blood into body tissue cells. Upsetting this balance causes many complications and pathologies including heart disease, coronary and peripheral artery sclerosis, peripheral neuropathies, retinal damage, cataracts, hypertension and coma and death from hypoglycemic shock.

In patients with insulin-dependent diabetes, the symptoms of the disease can be controlled by administering additional insulin (or other agents that have similar effects) by injection or by external or implantable insulin pumps. The "correct" insulin dosage is a function of the level of glucose in the blood. Ideally, insulin administration should be continuously readjusted in response to changes in blood glucose level. However, at present, blood glucose levels can only be determined directly by a blood sample. Unfortunately, since drawing the sample is invasive, blood glucose is usually only determined once daily or less often. As a result, insulin dosage is not optimally coordinated with blood glucose levels and complications can continue to be manifested. It would, therefore, be desirable to provide non-invasive means for more closely monitoring blood glucose levels and coordinating insulin dosages with such levels.

Many attempts have been made to develop a reliable less invasive or non-invasive way to measure blood glucose level. One of the most widely used methods has been measurement of glucose excreted in the urine, which is under certain conditions an indicator of blood glucose concentration. In its most convenient form, a "dipstick", which has been coated with chemical reagents, is dipped into a urine sample. Glucose in the urine then reacts with the chemical reagents on the dipstick to produce a color change which corresponds to the appropriate range of concentration. The level of urine glucose is then correlated with blood levels on the basis of statistical data and previous experience with the specific patient. However, urine testing has presented several drawbacks. Foremost, is the tenuous link between urine glucose level and blood glucose levels. Although general trends in blood levels within a certain range are usually reflected in urine levels, moderate or periodic fluctuations of blood levels may not be reflected in urine content. Therefore, any dosage change made on the basis of urine analysis is not finely-tuned to blood levels. Furthermore, other substances in urine can cause inaccuracy in measurement by interfering with chemical reactions necessary to produce the color change on the dipstick. Also, like blood sampling, urine analysis can only be performed at relatively widely spaced intervals when the patient produces urine for analysis.

Other systems have been proposed for monitoring blood glucose levels by implanting a glucose sensitive probe into the patient. Such probes have measured various properties of blood or other tissues, including optical absorption, electrochemical potential and enzymatic products. U.S. Pat. Nos. 4,436,094 and 4,704,029 disclose two examples of blood glucose level probes. U.S. Pat. No. 4,436,094 utilizes an implantable electrode which contains a charged carbohydrate species which, in the absence of glucose, is bound to a component of the electrode and does not affect the potential measured by the electrode. In the presence of glucose, however, charged carbohydrate is displaced from the binding component by molecules of glucose, and as a result of its charge, affects the potential measurement by the electrode. The measured potential can then be correlated to the concentration of glucose.

U.S. Pat. No. 4,704,029 discloses an implantable glucose monitor that utilizes a refractometer which measures the index of refraction of blood adjacent to an interface with the transparent surface of the refractometer by directing laser light at the interface to measure the index of refraction of the blood by the amount of radiation reflected at the interface. As the blood glucose concentration increases, the index of refraction of blood increases. By comparing the intensity of the light reflected by the blood with the intensity of light before contact in the blood, glucose concentration can be determined.

Another approach to tying blood glucose levels to insulin dosage has centered around the implantation of pancreatic cells which produce insulin in response to changes in blood glucose levels as shown for example in Altman et al., Diabetes 35:625-633 (1986); Recordi et al., Diabetes 35:649-653 (1986); Amsterdam et al., J. Cell Biol. 63:1037-1056 (1974); Brown et al., Diabetes 25:56-64 (1976); Carrington et al., J. Endocr. 109:193-200 (1986); and Sonerson et al., Diabetes 32:561-567 (1983). Altman et al. were able to maintain normal blood glucose levels in diabetic mice by implanting cells (1) in areas impermeable to antibodies, (2) suppressing the immunogenicity of the implantable cells in tissue culture before the implantation and (3) enclosing the cells in a capsule that was impermeable to antibodies. However, the implantation methods of Altman et al. and others are severely limited by the availability of large enough masses of cells for effective implantation by the ability to reliably get insulin production over extended periods after implantation.

SUMMARY OF THE INVENTION

A system and method have been developed that overcome the above-noted problems and also have numerous other advantages that will be apparent to those skilled in the art.

This invention relates to living cells that act as chemo-sensors. Chemo-sensors as used herein means any living cell that is sensitive to a specific constituent or a group of constituents. The invention makes use of the sensing properties of chemo-sensors that react by generating an electric, optical, or chemical signal so that the reaction can be monitored by sensing means of the system. Some cells, such as alpha and beta cells of the pancreas, respond to their natural stimuli by generating electrical signals.

It has been discovered that in some cases hormone secreting cells respond to stimuli by secreting a chemical substance that may be easier to detect than the chemical that initiates their reaction. Also, most cells, especially those that generate electrical signals, undergo changes in their optical properties that can be correlated with their electrical activity. These optical changes are generally in the form of changes in optical density, refringence, and/or reflectance, and the like. These optical changes can also be enhanced by applying voltage sensitive dyes to the external membrane of the cells.

The electrical or other response of the cells to the specific chemical may be used in the present invention to determine the concentration of the chemical. Making a determination according to this invention avoids the need to take blood or tissue samples from the patient in order to determine by chemical or physical analyses the concentration of the desired chemical. Invasive sample extraction has a strong inhibitory effect and should be avoided in many cases. The present invention provides a noninvasive alternative.

In accordance with the present invention, systems are disclosed which utilize implanted chemo-sensitive living cells to monitor blood, body or tissue chemical levels by monitoring their levels in bodily tissues in which they are implanted. The implanted cells produce detectable electrical, optical or other signals in response to changes in concentration in surrounding tissue. The signal is then detected and interpreted to give a reading indicative of the constituent blood or tissue levels. This reading can then be used as a basis for altering treatment such as drug dosage for injection, as a basis for giving instructions to an implanted pump to alter the amount of chemical or drug delivered by the pump, or as a basis for taking other corrective measures, such as altering diet. As a result, blood on body chemical levels can be more closely monitored and controlled in a noninvasive way and drug dosage can be more closely tailored with concomitant control of symptoms associated with disease.

A system for monitoring tissue and blood chemical constituent levels is disclosed which comprises chemo-sensitive cells which are capable of producing a signal in response to changes in chemical concentration in the medium surrounding the cells. The signal produced can either be electrical or optical. In certain embodiments, the cells are contained in a capsule which is constructed from a membrane or similar substance which is impermeable to large molecules such as antibodies, yet permeable to nutrients to keep the cells alive. The capsule can also be fitted with means for collecting the signals produced by the cells.

The present invention comprehends the use, broadly, of any living animal cells which are sensitive to the concentration of any chemical having a biological response in a patient's blood, body or tissues, and which produce signals proportional to concentration changes.

Broadly the system of the present invention is for monitoring the concentration of a chemical in a patient's blood, body or tissues. The said system comprises (a) implantable living animal cells that are sensitive to the chemical that is to be monitored, said animal cells being capable of producing an electrical, optical, or chemical signal in response to the chemical concentration in the medium surrounding said cells in the patient; and (b) means for detecting said electrical, optical, or chemical signal. The chemical may be a hormone such as sex-linked hormones, metabolism controlling hormones, steroids, and combinations thereof. In preferred embodiments, the signal is an electrical signal. The cells may be contained in a capsule, and the means for detecting said electrical, optical, or chemical signal may comprise collecting means in said capsule for collecting said electrical signal from said cells. Preferably, the collecting means are metal electrodes in contact with said cells such that said signal can be measured as a potential difference between said electrodes, and the means for detecting said electrical signal further comprises an implantable signal pickup device connected to said electrodes for processing said signal for transmission. The means for detecting said electrical signal may further comprise transmission means connected to said pickup device for transmitting said processed signal through a body surface.

Where the said signal is optical, the signal will preferably result from changes in the optical characteristics of said cells. The optical characteristics may be changed by dyes in or on the membranes of said cells that are affected by changes in the membrane potential of said membranes, and the means for detecting said optical signal may comprise an implantable optical sensing device positioned with respect to said cells so as to detect and process said signal for transmission. The means for detecting said optical signal may further comprise transmission means connected to said implantable optical sensing device for transmitting said processed signal through a body surface. Preferably, the means for detecting said electrical, optical or chemical signal comprises sensor means for detecting said transmitted signal through said body surface and for correlating said transmitted signal to said chemical concentration. In especially preferred systems, the sensor means comprises: (a) detector means for detecting said transmitted signal; (b) processor means connected to said detector means for correlating said transmitted signal to said chemical concentration; and (c) output means connected to said processor means for reporting said chemical concentration.

The system may comprise a pump connected to said pickup device such that said pump delivers a drug or chemical dosage appropriate to said chemical concentration. Preferably, the system further comprises a pump connected to the implantable optical sensing device of the means for detecting said electrical, optical or chemical signal, such that said pump delivers a drug or chemical dosage appropriate to said chemical concentration.

The cells may be selected from the group comprising beta cells, alpha cells and taste cells, preferably beta cells.

Another aspect of the present invention concerns a method of monitoring the concentration of a chemical in a patient's blood, body or tissues. The method may comprise: (a) implanting into said patient chemical sensitive living animal cells which are sensitive to the concentration of said chemical and capable of producing an electrical, optical, or chemical signal in response to said concentration of said chemical in the medium surrounding said cells in the patient; (b) detecting said signal; and (c) correlating said signal with said chemical concentration. The chemical may be a hormone selected from the group consisting of sex-linked hormones, metabolism controlling hormones, steroids, and combinations thereof. The signal may be detected through a body surface by an external signal sensor. Preferably, the signal is processed by said sensor and correlated with said corresponding chemical concentration. In especially preferred embodiments, the electrical or optical signal is detected by an implantable signal pickup device that processes said signal for transmission through a body surface, and the processed signal may be transmitted through said body surface and sensed externally thereof. The transmitted signal may be correlated with said corresponding chemical concentration.

Another aspect of the present invention concerns a method of administering a drug or chemical dosage, said method comprising (a) implanting into said patient chemical sensitive living animal cells capable of producing a signal in response to the concentration of a chemical in the medium surrounding said cells; (b) detecting said signal; (c) correlating said signal with said chemical concentration; and (d) administering said drug or chemical dosage at a level appropriate to said chemical concentration. Preferably the dosage is administered by an implanted drug or chemical pump.

In instances where the signal is electrical, these collecting means can be metal electrodes which are placed in contact with the cells such that the signal produced by the cells can be measured as a potential difference between the electrodes. The system can further include an implanted signal pickup device which is connected to the electrodes in the capsule for processing (e.g., amplifying and modulating) the signal for later transmission through the body surface, such as the skin, or for transmission to an external or implanted pump. Once the signal is processed the pickup device passes the signal on to means for transmitting the processed signal. In other embodiments, the implanted cells produce an electrical signal which can be detected by external electrodes without employing electrodes in the capsule or an implantable signal pick-up device.

Examples of chemicals or body constituents that chemo-sensors are sensitive to, as contemplated by the present inventions include, but are not limited to, electrolytes (ions of sodium, potassium, calcium, hydrogen, chloride, etc.); hormones (thyroid, steroids, insulin, glucagon, adrenaline, etc.); enzymes (ATP, dehydrogenase, lipases, tripsin, etc.); carbohydrates (various sugars such as glucose, fructose, manose, sucrose, etc., glycogen, etc.); lipids (cholesterol, lipid acids, high and low density lipids, etc.); amino acids, peptides and proteins (albumins, polypeptides, globulons, antibodies, various antigens, etc.); toxins (endotoxins, pertusis toxin, tetanus, toxin, etc.); transmitters (acetyl choline, GABA, etc.); drugs; volatile substances that are recognized as smell (alcohols, ethers, esters, etc.); water dissolved substances that are recognized as taste (sugars, carbohydrates, amino acids, etc.); dissolved gases ($O_2$, $CO_2$, nitrogen, carbon monoxide, hydrogen, etc.)

In instances where the signal is optical, the signal is produced by a change in the optical qualities of the cells or specifically the membranes of the implanted cells. Preferably, the signal is produced by dyes contained within or coated on cellular membranes which will change the optical properties of the cell in response to changes in electrical activity of the cell. This change in optical quality can be detected through relatively transparent body surfaces, such as thin skin layers or fingernails. Alternatively, the optical change can be measured by an implanted optical detector, i.e., a photosensor-phototransistor coupled with a light source such as a light emitting diode. The optical signal can be fluorescence. The optical detector can process the detected signal much as the implanted pick-up device previously described processes electrical signals. The processed signal can be used to control a pump or transmitted through the skin for external detection. A chemical signal emitted by the chemo-sensor cells can be detected by photometric means, as a potential difference generated by an appropriate membrane coated electrode, or the like.

The electrical signal or the optical signal are detected through the skin by an external sensor and then correlated to a corresponding blood constituent level. The sensor includes means for detecting the signal, means for processing such signal and correlating it to the corresponding blood or tissue levels, and output means for reporting or relating the level as determined.

Alternatively, the implanted signal pickup device can pass a processed signal on to an implanted pump, which, in response to such signal, delivers an appropriate dosage of chemical or drug corresponding to the determined blood or tissue level.

Capsules for use in practicing the present invention are also disclosed which comprise a membrane which is impermeable to large molecules such as antibodies and is permeable to nutrients necessary for cell growth. Chemo-sensitive cells are enclosed within the membrane, along with electrodes in contact with the cells such that changes in the electrical activity of the cells can be detected as a potential difference between the electrodes.

Another aspect of the present invention concerns a capsule that comprises (a) a membrane which is impermeable to large molecules such as antibodies and is permeable to nutrients necessary for cell growth; (b) chemo-sensitive cells enclosed within said membrane; and (c) electrodes in contact with said cells such that changes in the electrical activity of said cells can be detected as a potential difference between said electrodes. The capsule may comprises: (a) a membrane which is impermeable to large molecules such as antibodies and is permeable to nutrients necessary for cell growth; (b) chemo-sensitive cells enclosed within said membrane; and (c) means for shorting out the interior of said capsule with respect to the exterior of said capsule such that electrical activity of said cells is dissipated on said exterior. The capsule may also comprise: (a) a membrane which is impermeable to large molecules such as antibodies and is permeable to nutrients necessary for cell growth; and (b) chemo-sensitive cells enclosed within said membrane, wherein said cells have been treated such that the cellular membranes of said cells contain or are coated with dyes which are sensitive to changes in cellular membrane potential.

Alternatively, in place of the electrodes, the capsules can enclose means for "shorting-out" the interior of the capsule with respect to the exterior of the capsule such that the electrical activity of the cells is optimally dissipated on the exterior of the capsule. As a result, the electrical activity will be maintained at a level which can be detected by appropriate sensing means.

Capsules are also disclosed which contain chemo-sensitive cells which have been treated such that the cellular membranes of the cells are coated with dyes which are sensitive to change in cellular membrane potential.

Finally, methods of monitoring the blood constituent level employing the capsules and systems of the present invention are disclosed. Basically, those methods comprise implanting into the patient chemo-sensitive cells, detecting the signal produced by the cells in response to levels and/or changes in the concentration of the specific constituent and correlating that signal with the corresponding blood or tissue level. Methods of administering the constituent when needed are also disclosed which comprise administering the constituent (or other correcting agent) appropriate to the blood level determined in accordance with the methods disclosed herein. Such agent can be either administered manually or by operation of an external or implanted pump which is connected to the detecting and monitoring system. In cases where the agent is insulin, other therapeutic agents that alter blood glucose levels may be substituted therefore, such as "DIA BETA" (glyburide; Hoechst-Roussel), "GLOCONTROL" (glipizide; Pfizer) and "DIABINESE" (chlorpropamide; Pfizer).

Other features and advantages of this invention will be apparent to those skilled in the art.

BRIEF DESCRIPTION OF THE FIGURES

To facilitate further discussion of this invention, the following figures are provided in which:

FIG. 2 depicts bursts of spiked electrical activity produced by pancreatic beta cells in response to various glucose concentrations;

FIG. 8 depicts one embodiment of a system of the present invention that utilizes an optical signal.

The figures are for illustrative purposes only and should not be used to unduly limit the scope of the invention.

DETAILED DESCRIPTION OF THE INVENTION

Figure 1:
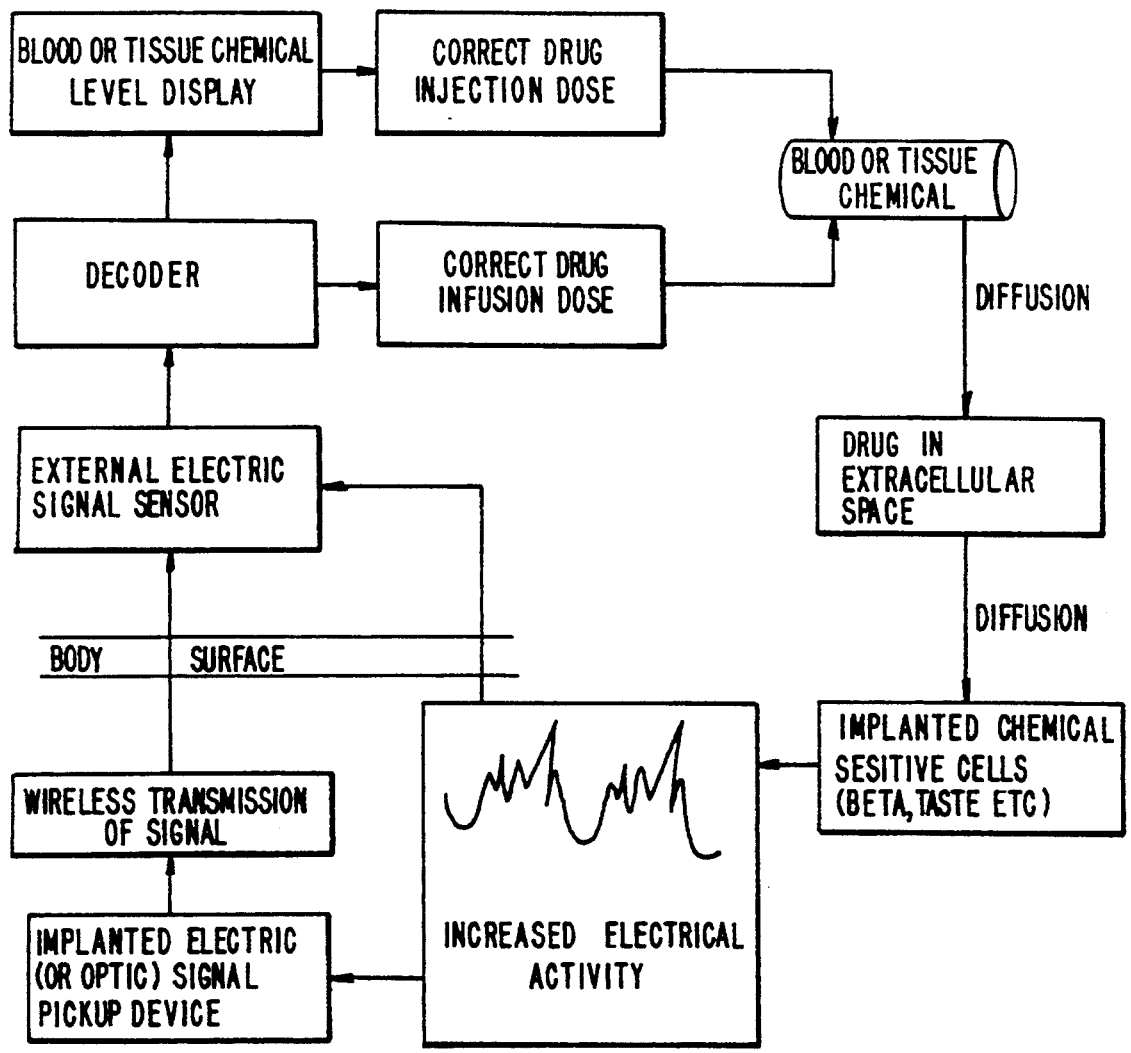
FIG. 1 is a schematic representation of the components and operation of a system of the present invention.
Figure 3A:
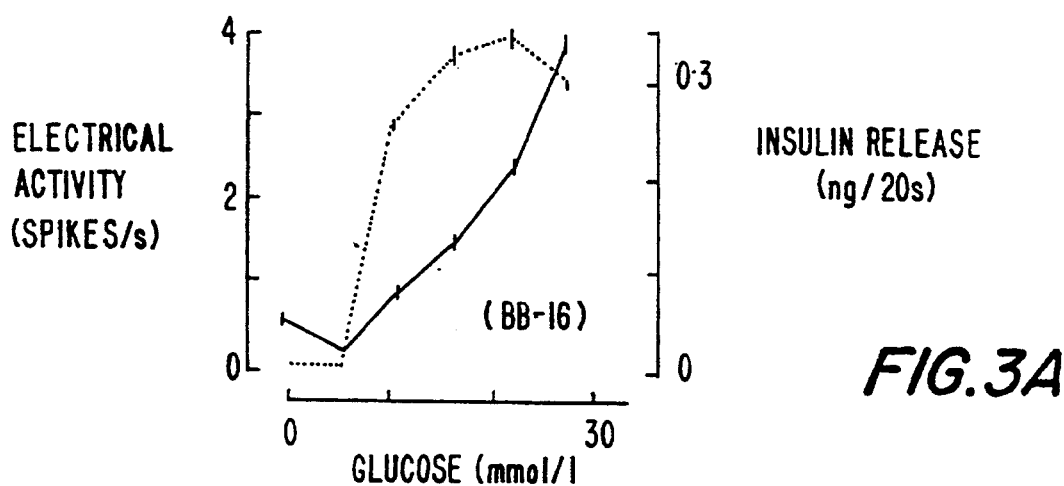
FIG. 3 contains graphs of electrical activity of six different preparations of beta cells in response to varying glucose concentration.
Figure 3B:
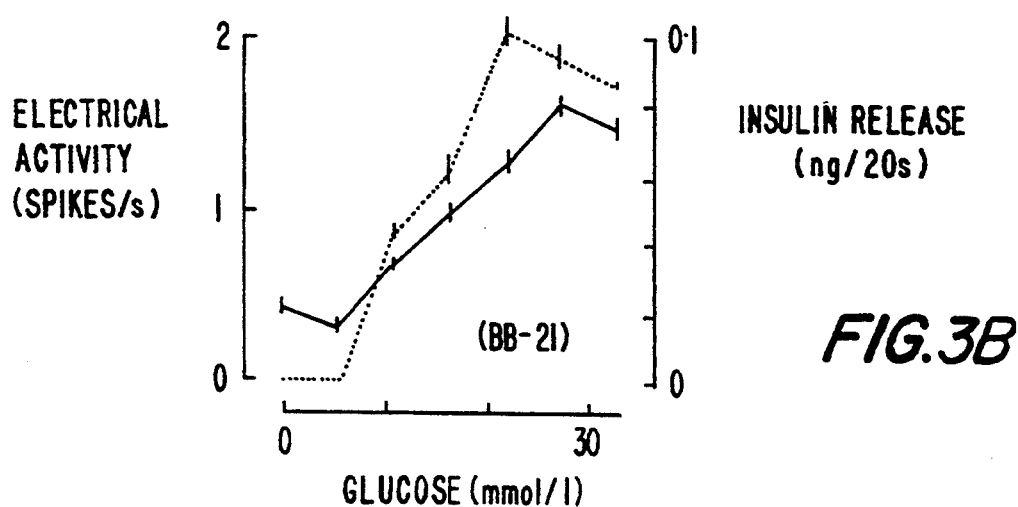
Figure 3C:
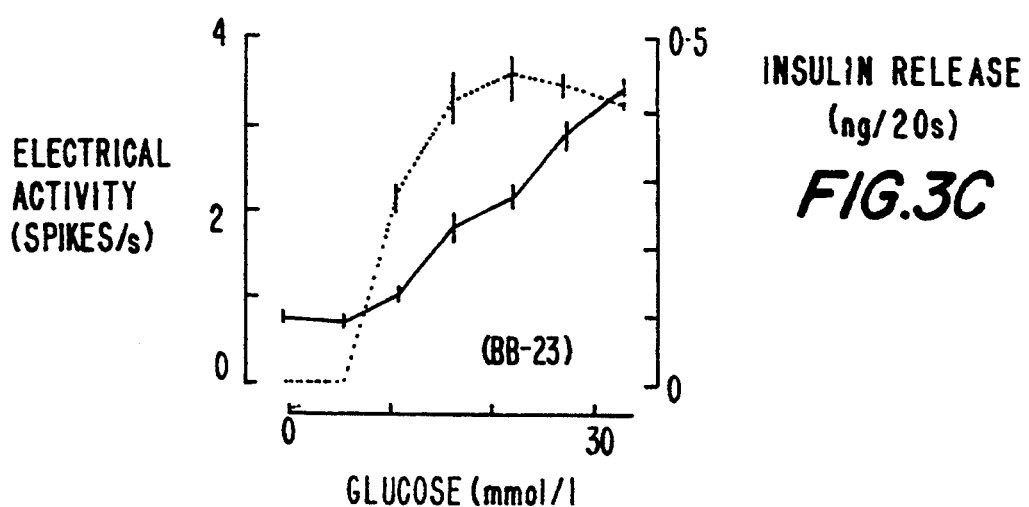
Figure 3D:
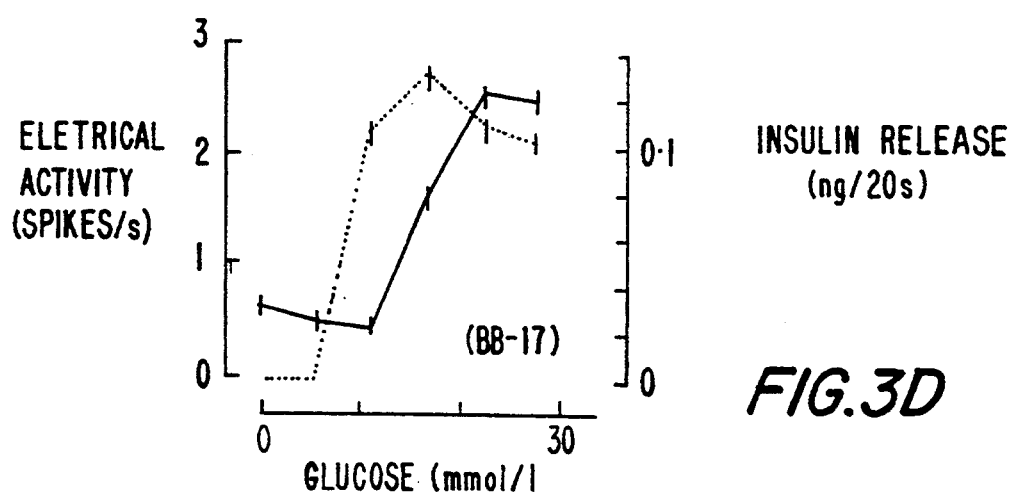
Figure 3F:
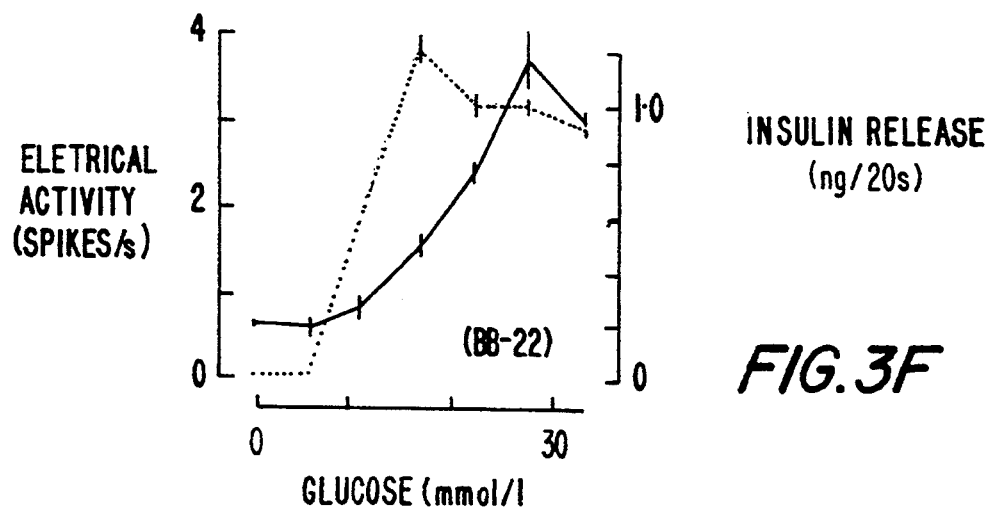
Figure 3E:
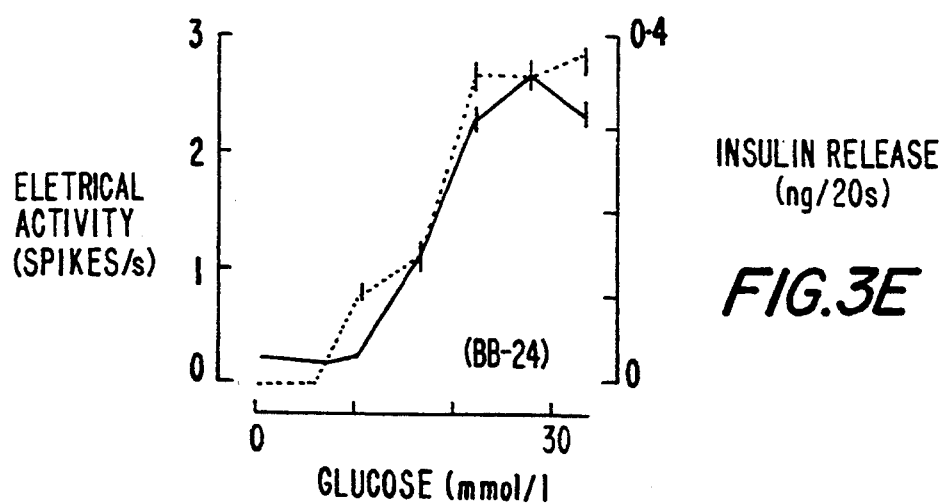

FIG. 1 schematically describes one embodiment of a system of the present invention which is described in further detail below. As shown at the upper right of FIG. 1, the selected chemical constituent diffuses from the bloodstream into the extracellular space in bodily tissues. Eventually the material diffuses to implanted chemo-sensitive cells which are a part of the system of the present invention. The implanted cells respond by exhibiting electrical activity, such as a change in membrane potential, commensurate with the concentration of the constituent in the extracellular space.

The electrical activity can be detected or monitored in one of two ways. Where the electrical activity is strong enough to be detected through a body surface (e.g., layers of skin), the electrical activity is detected directly by an external signal sensor. Alternatively, the electrical activity is monitored by an implanted signal pickup device. The pickup device processes and amplifies the electrical activity. The amplified signal is then transmitted through a body surface (such as the skin) and is detected by the external signal sensor.

The external signal sensor contains or is connected to a decoder or microprocessor that interprets the signal. The decoder correlates the signal with blood concentration of the specific chemical on the basis of an algorithm and programmed information relating to the correlation between blood concentration levels and concentration at the implantation site for the patient in which the system is implanted. For example, the microprocessor can be programmed to correlate a constituent concentration of 20 MM at the implantation site with a concentration of 22 MM in the blood on the basis of prior and periodic blood sampling. Once the signal has been correlated and translated into a reading of the blood concentration, the concentration information is used in one of two ways. First, the information can be displayed for reading by the patient or a person caring for the patient. On the basis of the displayed concentration, the correct chemical or drug dose can be administered or diet can be adjusted. Alternatively, the concentration information is fed into a pump, external or implanted, that infuses the correct dosage on the basis of the determined blood concentration level. The concentration information can also be fed to other devices (such as automatic liquid infusion apparatus) which will take corrective action on the basis of such information.

The systems of the present invention utilize chemosensitive living cells as sensors of the blood constituent levels either directly (by implantation in the bloodstream) or indirectly (by implantation in tissues in equilibrium with blood concentration levels). Any cell type that produces a detectable electrical activity in response to changes in concentration of the specific chemical in the surrounding environment can be used in practicing the present invention.

For example, Beta cells from the islets of Langerhans in the pancreas are preferred glucose sensitive cells. Beta cells have been shown to produce electrical activity, action potentials, in response to glucose concentration and have the advantage that they respond properly to glucose in the concentration range relevant to patient monitoring. Scott et al., Diabetologia 21:470–475(1981); Pressel et al., Biophys. J. 55:540a (1989); Hidalgo et al., Biophys. J. 55:436a (1989); Atwater et al., Biophys. J. 55:7a (1980). Beta cells respond to glucose in bursts of spikes of electrical activity. The spike frequency, burst duration and pauses between bursts are all functions of glucose concentration. FIGS. 2 and 3 present data relating to the electrical activity of beta cells. As shown in FIG. 2, the burst duration increases as glucose concentration increases. The pause between bursts also decreases as glucose concentration increases. In FIG. 3, the spike frequency (spikes/second) increases as glucose concentration increases. Each of these parameters (burst duration, pause duration and spike frequency), as well as spike shape, can be monitored alone or in combination as a source of signal corresponding to cellular electrical activity. It has also been established that the beta cells are electrically coupled, resulting in synchronized electrical activity of the cells. Eddiestone et al., J. Membrane Biol. 77:1–141 (1984), Meda et al., Quarterly J. Exper. Physiol. 69:719–735 (1984). Therefore, in response to a change in the glucose concentration, many cells fire their action potentials or electrical signals in synchrony, producing a significantly amplified signal which is easier to detect.

Methods for isolating cells such as chemo-sensitive cells are described in the references cited in the preceding paragraph and in Amsterdam et al., J. Cell Biol. 63:1037–1056 (1979); Ricordi et al., Diabetes 35:649–653 (1986); and Carrington et al., J. Endocr. 109:193–200 (1986). In addition, any other method for isolating such cells can be used which preserves the ability of the isolated cells to respond to changes in the chemical concentration. Methods for culturing pancreatic cells are disclosed in Amsterdam et al., J. Cell Biol. 63:1037–1073 (1974); Amsterdam et al., Proc. Natl. Acad. Sci. USA 69:3028–3032 (1972); Ciba Foundation Symposium on the Exocrine Pancreas, Reuck and Cameron, ed., p. 23–49 (J. and A. Churchill Ltd., London 1962); and Howard et al., J. Cell. Biol. 35:675–684 (1967).

Chemical sensor cells in taste buds have also been shown to respond to fluctuations in glucose, salts and other ingredient concentration. Ozeki, J. Gen. Physiol. 58:688–699 (1971); Avenet et al., J. Membrane Biol. 97:223–240 (1987); Tonosaki et al.; Brain Research 445:363–366 (1988). Taste cells show particular advantage for systems of the present invention because under suitable conditions such cells regenerate every few days by continuous division. Thus, prolonged growth of these cells when implanted is more readily sustained. Taste cells are also more accessible than other cells. A sample of taste cells can be removed from a patient with only minor surgery, grown in culture to obtain a sufficient number of cells and then implanted. The ability to use a patient's own cells also reduced the likelihood of immunologic reactions to the implant. Taste cells can be isolated according to the methods of the publications cited above or by any other method which preserves the ability of the cells to respond to a change in various chemical concentrations, such as changes in concentrations of amino acids, sucrose, salts, esters, and the like.

Alpha cells from the pancreas have been shown to be sensitive to glucose as well as other constituent concentrations in the surrounding medium. Sonerson et al., Diabetes 32:561–567 (1983). Transformed cell lines, such as the insulin producing line disclosed in U.S. Pat. No. 4,332,893, and hydridoma lines can also be used. Any electrical activity associated with the response by alpha cells or transformed lines can be harnessed in practicing the present invention.

Many methods are known, for example, for implanting beta cells in human tissues. Altman et al., Diabetes 35:625–633 (1986); Ricordi et al., Diabetes 35:649–653 (1986); Brown et al., Diabetes 25:56–64 (1976); Schmidt et al., diabetes 32:532–540 (1983). Other means for encapsulating living cells are disclosed in U.S. Pat. Nos. 4,663,286, 4,409,331, 4,352,883, 4,798,786, 4,689,293 and 4,353,888. Although the implanted cells of the present invention need not necessarily be encapsulated, any of these methods can be employed to produce an implantable capsule where such is used. The method of Altman et al. is preferred. the Altman capsule is a thin walled (about 100 microns thick) tube or elongated pellet made of a polyvinyl chloride acrylic copolymer, with a diameter of about 1 mm. These dimensions or even smaller dimensions are preferred to maintain proper diffusion to all cells. The molecular-weight cut off of the Altman et al. capsule membrane was approximately 50,000. In preferred embodiments of the present invention, the cut off is less than 50,000 and most preferably between 1,000 and 10,000.

The capsule will typically comprise groups of from about 2,000–50,000 individual cells, preferably from about 7,500–12,500, within an islet. The diameter of the capsule will typically be from about 0.05–1.0 mm, preferably from about 0.1–0.4 mm, and preferably about 0.2 mm in diameter.

The capsule serves two basic functions. First, it serves as a barrier that prevents the cells from migrating away, while nutrients and waste products are free to diffuse through the capsule. Second, it serves to prevent antibodies and other large molecules from leaving or entering the capsule, for example, to prevent immunological reactions. The capsule also allows the use of chemo-sensitive tumor cell lines as sensor cells which must be contained to prevent proliferation. Any material which will provide these functions can be used to form capsules containing chemo-sensitive cells.

In some embodiments, while not significantly interfering with production and detection of cellular electrical activity, the capsules are equipped with means for aiding detection of cellular electrical activity, such as electrodes or conducting bars that short-circuit the cell electrical activity with the outside. The capsules are also preferably implanted in clusters as to ensure a detectable signal even if one or more capsules becomes dysfunctional. The capsules may also contain means to fix them in the desired location or materials useful for determining the location of the capsules, such as radio-opaque materials.

Where the electrical activity is too low to be detected through the body surface without amplification or where the electrical activity is to be harnessed to drive an insulin pump, electrodes are placed on the inside of the capsule such that a potential difference can be measured across the electrodes which corresponds to the electrical activity of the cells inside the capsule. The prevent cell damage, these should be made from an inert metal, such as those commonly used in a variety of implants. See for example, "Cardiac Pacing and Physiology," Proceedings of the VIIIth World Symposium on Cardiac Pacing and Electrophysiology, Jerusalem, Israel, Jun. 2–11, 1987, ed. Belhassen et al., (Keterpress Enterprises, Jerusalem); IEE Trans. Biomed. Eng. 34:664–668 (1987); and J. Am. Coll. Cardiol. 11:365–370 (1988). Since these electrodes are used for signal pickup only and not for electric stimulation, their functional lifetime should be practically indefinite. The electrodes are connected by insulated wires to an implanted signal pickup device for processing and amplification or to the drug or chemical dispensing pump.

Figure 6A:
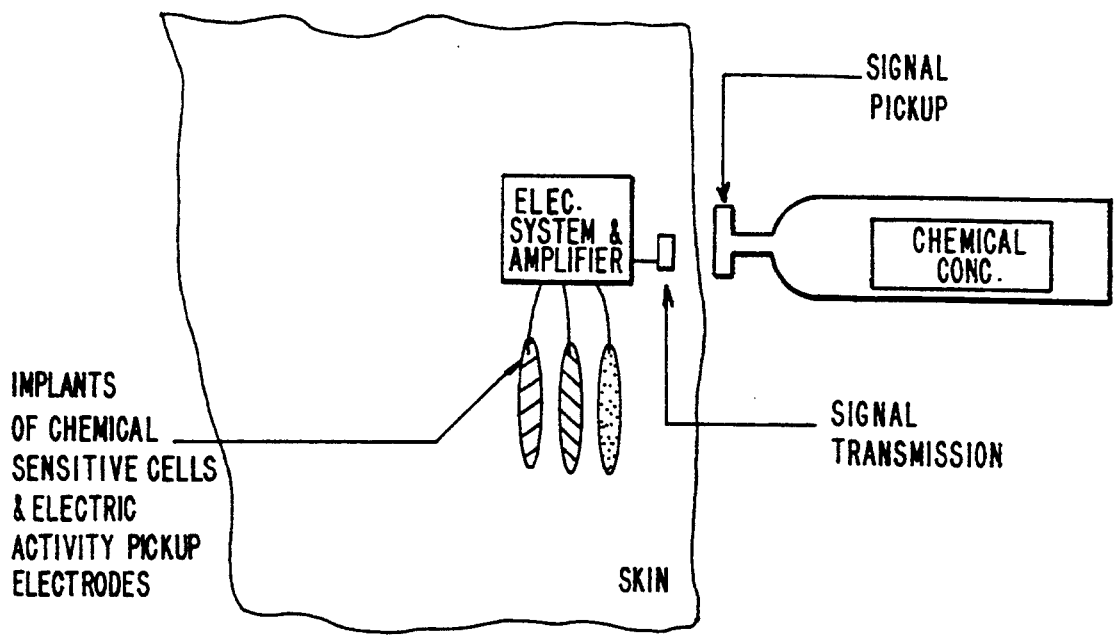
FIGS. 6A, 6B and 7 depict possible arrangements of the components of a system of the present invention with respect to the skin.
Figure 6B:
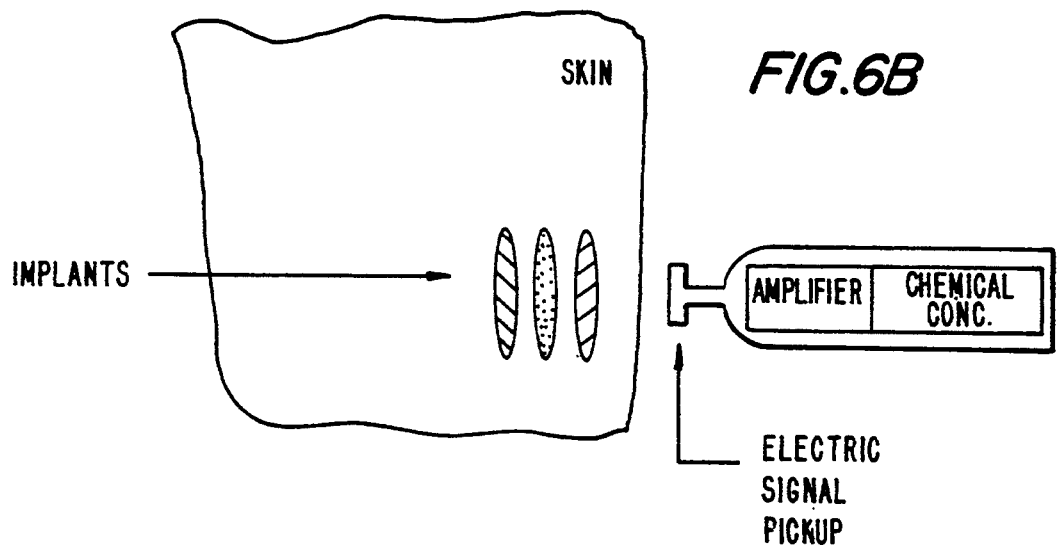

First, where the electrical activity of the implanted cells generates electrical signals strong enough to be picked up from the external body surface by electrodes (as in EEG or ECG), the capsules are implanted near the surface of the skin where the skin is very thin and the location convenient. As shown in FIG. 6B, the signal is then detected by the external signal sensor. Alternatively, where the electrical activity is too small to be picked up by external means, electrodes are introduced into the capsule and connected to the implanted signal pickup device as shown in FIG. 6A. In this case the capsule implantation can be done anywhere in the body, for example, the peritoneal cavity where implantation is relatively easy and vascularization is adequate.

Figure 5:
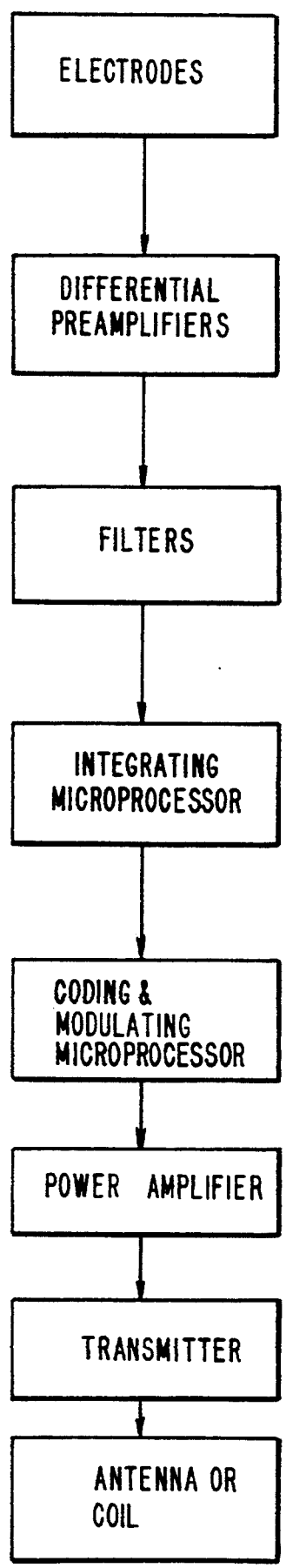

The basic components of the implanted signal pickup device are shown in FIG. 5. Basically, the device resembles implanted pacemakers in its external surface property. It can contain some or all of the following elements as necessary to provide a processed signal which is suitable for transmission or other desired use:

1. Inputs connected to the electrodes inside the implanted capsules.
2. A number of low noise, high input impedance differential preamplifiers corresponding to the number of capsules. Preferably, each capsule is connected to a single differential input amplifier.
3. Band pass filters at the outputs of the amplifiers. In certain embodiments, each amplifier may be connected through two filters, one designed to pass only the spikes (action potentials) while the other will pass only the very slow potential shifts associated with each burst of activity.
4. An integrating amplifier or microprocessor that sums up the output of all the preamplifiers.
5. A coding and modulating microprocessor that processes the summed signal so as to be best suitable for transmission across the skin, such as FM modulation.
6. A power amplifier that boosts the processed signal and is connected to the transmitter that sends the processed signal through the skin.

There are two preferred alternative modes of transmission of the data from the internal implanted amplifier across the skin to the external sensor. In the first alternative, the amplifier is driven by low amplitude local currents by means of a pair of electrodes implanted under the skin. The electric field thus created is similar to those generated by the heart (such as in ECG measurement) and can be detected similarly by external electrodes. AC modulation of these currents will prevent local tissue stimulation, electrode polarization, and the like. In the second alternative, the output of the amplifier is fed, after proper modulation, to an induction coil or a coupling capacitive signal transferor. This coil generates an electromagnetic field that is picked up by a similar externally positioned coil. Other means for transmitting a signal across the tissue barrier will be apparent to skilled artisans and may be used in practicing the present invention.

Figure 4:
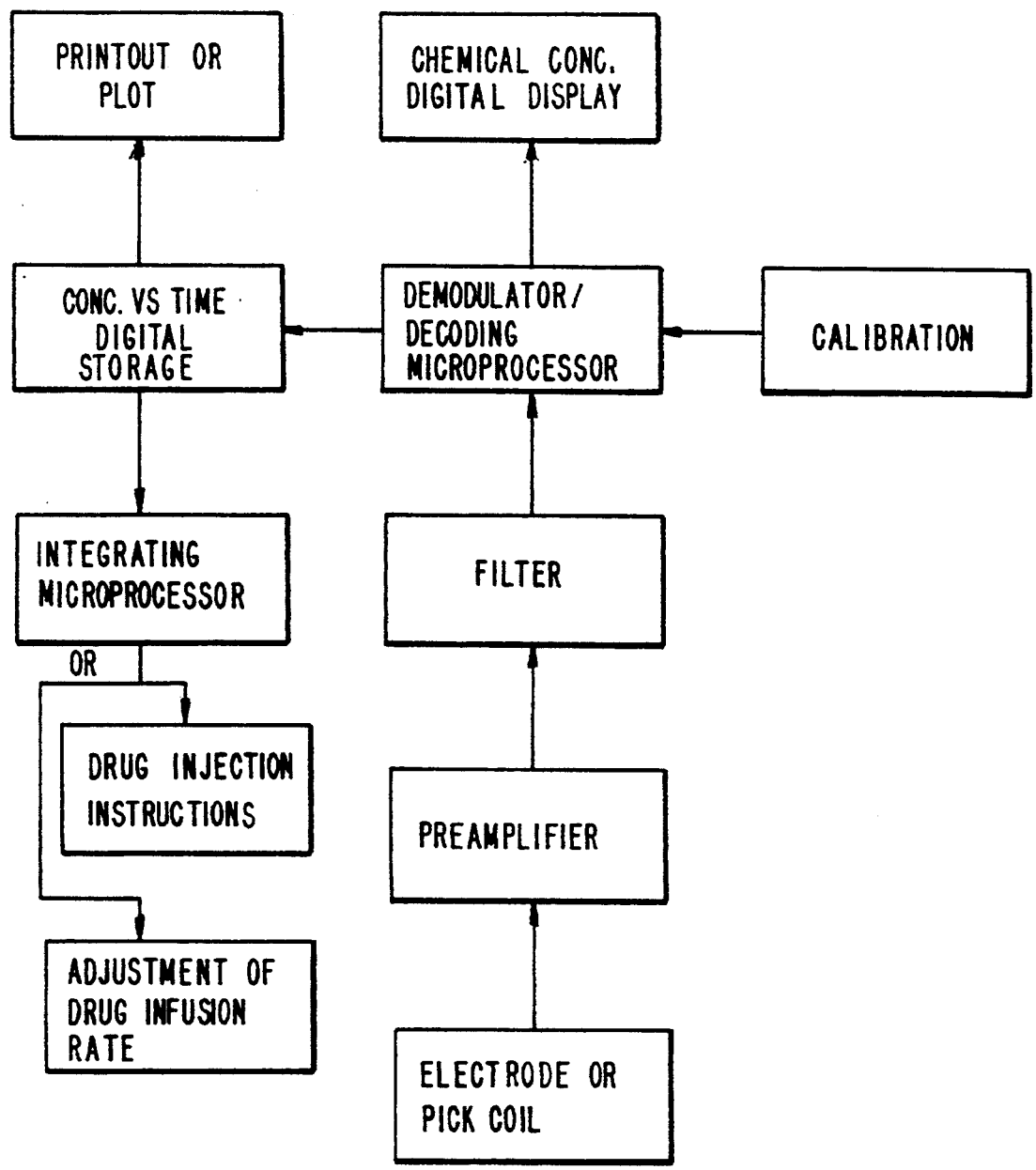
FIGS. 4 and 5 are schematic representations of the electrical components of systems of the present invention.

The signal from the capsules or the transmitter of the signal pickup device is detected by an external signal sensor. The basic components of the signal sensor are shown in FIGS. 4 and 6. In certain embodiments, the signal sensor can include one or more of the following elements:

1. A sensor, such as an electrode, coil or other means suited to detect the electrical or optical signal transmitted through the body surface.
2. A preamplifier connected to the sensors (which may not be necessary where the signal is already amplified before transmission across the skin barrier).
3. A filter for external noise reduction.
4. A demodulator—decoding microprocessor that separates the signals from their FM carrier or other modulation means when such a mode of transmission is used.
5. A signal processor that utilizes the appropriate algorithms and programmed information relating to the constituent concentration to translate the transmitted signal into the corresponding concentration.

The processed and decoded signal corresponding to determined constituent concentration is then passed on to means for outputting such information in the desired manner. For example, the concentration information can be presented as a digital readout in the form of a digital display on the probe itself or a display and printout in an associated device. A memory may be used to save the concentration values obtained during continuous or frequent concentration monitoring. Such information may also be used for determination of the correct amounts of constituent or drug to be taken by the patient or determining patient diet. Such information can be displayed for patient use or as an input to an automated infusion device.

A calibration system can also be associated with the system of the present invention. Since the exact dependency of electrical activity of the implanted cells on the chemical concentration may vary with time, a means for recalibration of the system is provided. Upon calibration the external device or probe is put into calibration mode. The current blood concentration level, as determined by a blood sample or other reliable means is fed manually (or automatically) to the calibration circuit that will reset the proper parameters of the concentration determining algorithms. A second determination may be necessary at times to obtain two points on the calibration curve. Calibrations can be performed as frequently or infrequently as necessary to achieve and maintain the desired degree of accuracy in the determination.

Figure 7:
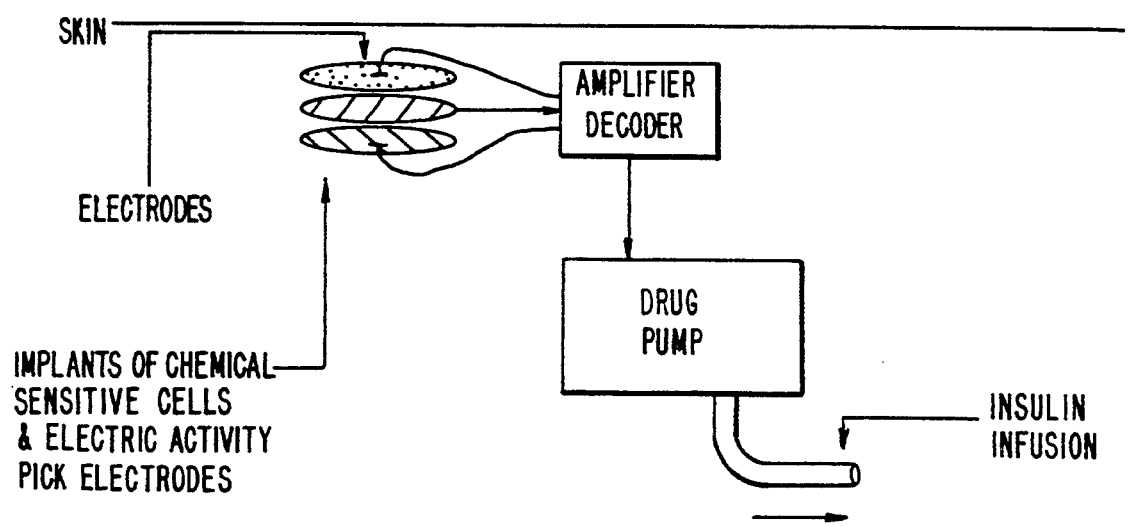

As shown in FIG. 7, in certain embodiments the processed signal is used to control an implanted infusion pump. By means of the controller the pump output is kept relatively consistent with the blood levels thus allowing the pump to more closely mimic the human normal response and control. Most commercially available implantable infusion pumps can be adapted for such use giving the pump similar properties to those of the sensor cells.

An alternate embodiment of a system of the present invention converts the electrical activity of the chemosensitive cells into an optical signal. Direct changes in cell optical properties resulting from electrical activity can be measured as an optical signal. Alternatively, biocompatible dyes which are sensitive to electric fields can be incorporated into the cell membranes and subjected to the membrane potential or electrical field. Dyes useful for practicing this embodiment are disclosed in Grinvald et al., Physiol. Rev. 68:1285-1366 (1988) and Gross et al., Biophys. J. 50:339-348 (1986). Other suitable dyes include those commercially available from Molecular Probes, Inc., Eugene, Oreg. The changes in the membrane potential induce changes in the optical properties of untreated cells or dyed cells, for example, in the optic density, fluorescence or birefringence of the cell membranes. Thus, the action potentials or electric spikes that the cells generate in response to the constituent concentration induce changes in the optical properties of the cells (i.e., they generate optical signals). These signals are picked up by an implanted or external optic sensor. In certain embodiments, the cells are implanted such that a transparent body surface, such as thin skin layers or fingernails, separates them from the outside world. In optical signal embodiments, if a capsule is used, it must be constructed from a material through which the optical changes can be stimulated and measured (e.g., practically all thin plastics). One such implantation of cells is shown in FIG. 8. As shown, an external optical sensor monitors the cell activity and translates it into concentration data. The external sensor can include a light source of the proper wavelength to excite the dyes or to be reflected from the cell surfaces and other components previously described for the external electrical signal sensor for processing, decoding and outputting the signal. Alternatively, the optical sensing components can be implanted such that an electrical signal, corresponding to the optical signal, is produced which can be detected or transmitted through the skin.

Variations and modifications will be apparent to those skilled in the art and the claims are intended to cover all such variations and modifications that fall within the true spirit and scope of the invention.

All of the documents identified herein, including patents and patent applications, are incorporated herein by reference in their entireties for all purposes.

I claim:

1. A system for monitoring the concentration of a chemical in a patient's blood, body or tissues, said system comprising:
   implantable living animal cells that are sensitive to said chemical, said animal cells being capable of producing an electrical, optical, or chemical signal in response to the chemical concentration in the medium surrounding said cells in the patient; and
   means for detecting said electrical, optical, or chemical signal.

2. The system of claim 1 wherein the animal cells are sensitive to the concentration of a chemical having a biological response in the patient's blood, body or tissues.

3. The system of claim 1 wherein said chemical is a hormone.

4. The system of claim 1 wherein said signal is an electrical signal.

5. The system of claim 4 wherein said cells are contained in a capsule and wherein the means for detecting said electrical, optical, or chemical signal comprises collecting means in said capsule for collecting said electrical signal from said cells.

6. The system of claim 5 wherein said collecting means are metal electrodes in contact with said cells such that said signal can be measured as a potential difference between said electrodes.

7. The system of claim 1 wherein said signal is optical.

8. The system of claim 7 wherein said signal results from changes in the optical characteristics of said cells.

9. The system of claim 8 wherein said optical characteristics are changed by dyes in or on the membranes of said cells that are affected by changes in the membrane potential of said membranes.

10. The system of claim 8 wherein the means for detecting said optical signal comprises an implantable optical sensing device positioned with respect to said cells so as to detect and process said signal for transmission.

11. The system of claim 10 wherein the means for detecting said optical signal further comprises transmission means connected to said implantable optical sensing device for transmitting said processed signal through a body surface.

12. The system of claim 1 wherein the means for detecting said electrical, optical or chemical signal comprises sensor means for detecting said signal through a patient's body surface and for correlating said signal to said chemical concentration.

13. The system of claim 12 wherein said sensor means comprises:
   detector means for detecting said signal;
   processor means connected to said detector means for correlating said signal to said chemical concentration; and
   output means connected to said processor means for reporting said chemical concentration.

14. The system of claim 1 wherein said cells are selected from the group consisting of beta cells, alpha cells, taste cells, and combinations thereof.

15. The system of claim 14 wherein said cells are beta cells.

16. A method of monitoring the concentration of a chemical in a patient's blood, body or tissues, said method comprising:
   implanting into said patient chemical sensitive living animal cells which are sensitive to the concentration of said chemical and capable of producing an electrical, optical, or chemical signal in response to said concentration of said chemical in the medium surrounding said cells in the patient;

detecting said signal; and correlating said signal with said chemical concentration.

17. The method of claim 16 wherein the animal cells are sensitive to the concentration of a chemical having a biological response in the patient's blood, body or tissue.

18. The method of claim 16 wherein said chemical is a hormone.

19. The method of claim 16 wherein said signal is detected through a body surface by an external signal sensor.

20. The method of claim 19 wherein said signal is processed by said sensor and correlated with said corresponding chemical concentration.

21. The method of claim 16 wherein the electrical or optical signal is detected by an implantable signal pickup device that processes said signal for transmission through a body surface.

22. The method of claim 21 wherein said processed signal is transmitted through said body surface and is sensed externally thereof.

23. The method of claim 22 wherein said transmitted signal is correlated with said corresponding chemical concentration.

24. A method of administering a drug or chemical dosage, said method comprising:

implanting into said patient chemical sensitive living animal cells capable of producing a signal in response to the concentration of a chemical in the medium surrounding said cells;

detecting said signal;

correlating said signal with said chemical concentration; and administering said drug or chemical dosage at a level appropriate to said chemical concentration.

25. The method of claim 24 wherein said chemical is a hormone.

26. The method of claim 24 wherein said dosage is administered by an implanted drug or chemical pump.

* * * * *